(12) United States Patent
Kavermann et al.

(10) Patent No.: US 10,828,445 B2
(45) Date of Patent: Nov. 10, 2020

(54) TRACHEOSTOMY GUARD

(71) Applicant: Fisher & Paykel Healthcare Limited, Auckland (NZ)

(72) Inventors: Stephen William Kavermann, Auckland (NZ); Andrew Chi Lup Lau, Auckland (NZ); Andrew Paul Maxwell Salmon, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1086 days.

(21) Appl. No.: 15/217,569

(22) Filed: Jul. 22, 2016

(65) Prior Publication Data

US 2017/0049982 A1 Feb. 23, 2017

Related U.S. Application Data

(60) Provisional application No. 62/196,661, filed on Jul. 24, 2015, provisional application No. 62/329,638, filed on Apr. 29, 2016.

(51) Int. Cl.
*A61M 16/04* (2006.01)
*A61M 16/08* (2006.01)

(52) U.S. Cl.
CPC ..... *A61M 16/0465* (2013.01); *A61M 16/0463* (2013.01); *A61M 16/0488* (2013.01); *A61M 16/0816* (2013.01)

(58) Field of Classification Search
CPC .......... A61M 16/0465; A61M 16/0463; A61M 16/0488; A61M 16/0816; A61M 16/047; A61M 2039/0279; A61M 2039/0276; A61M 2039/0264; A61M 2039/0288
See application file for complete search history.

(56) References Cited

U.S. PATENT DOCUMENTS

| 3,912,795 | A | * | 10/1975 | Jackson | A61M 16/04 128/203.12 |
| 4,235,229 | A | | 11/1980 | Ranford et al. | |
| 4,240,417 | A | * | 12/1980 | Holever | A61M 16/0465 128/203.12 |
| 4,802,474 | A | * | 2/1989 | Beevers | A61M 16/047 128/200.26 |

(Continued)

FOREIGN PATENT DOCUMENTS

| CN | 2661200 | 12/2004 |
| WO | WO 84/02657 | 7/1984 |

(Continued)

OTHER PUBLICATIONS

Hudson RCI, Comfort Flo Plus Brochure; dated Nov. 2015.

(Continued)

*Primary Examiner* — Timothy A Stanis
*Assistant Examiner* — Cana A Gallegos
(74) *Attorney, Agent, or Firm* — Knobbe, Martens, Olson & Bear, LLP

(57) ABSTRACT

A tracheostomy guard couples with a patient interface to reduce the risk of occlusion of the patient interface. The tracheostomy guard has features that may prevent accidental disconnection from the patient interface while enabling suction to be applied to a patient. The tracheostomy guard may prevent patient secretions from being communicated with a caregiver in use.

23 Claims, 11 Drawing Sheets

(56) References Cited

U.S. PATENT DOCUMENTS

| | | | |
|---|---|---|---|
| D309,021 S * | 7/1990 | Beevers | D24/110 |
| 5,300,043 A * | 4/1994 | Devlin | A61M 1/0043 604/250 |
| 5,520,174 A | 5/1996 | Evans et al. | |
| 6,516,803 B1 * | 2/2003 | Enzinger | A61M 16/201 128/207.16 |
| 2004/0177851 A1 * | 9/2004 | Acosta | A61M 16/0465 128/207.14 |
| 2007/0181130 A1 * | 8/2007 | Worley | A61M 16/0465 128/207.14 |
| 2009/0032028 A1 * | 2/2009 | Bare | A61M 16/0468 128/207.16 |
| 2010/0071693 A1 * | 3/2010 | Allum | A61M 16/04 128/203.27 |
| 2011/0067699 A1 * | 3/2011 | Caruso | A61M 16/0463 128/205.29 |
| 2014/0238389 A1 | 8/2014 | Bruggemann et al. | |

FOREIGN PATENT DOCUMENTS

| | | |
|---|---|---|
| WO | WO 2015/021405 | 2/2015 |
| WO | WO 2015/033263 | 3/2015 |

OTHER PUBLICATIONS

Optiflow Tracheostomy Interface Marketing Materials, Fisher & Paykel Healthcare Limited, 2011.
Optiflow Tracheostomy Direct Connection OPT970, Fisher & Paykel Healthcare Limited, 2016.
BMS, Tilson Trach Guard; 2015; Beevers Medical Solutions; http://www.beevers.net/our-products/tilson-trach-guard.
Presentation to BME Students; Fisher & Paykel Healthcare Limited; Mar. 10, 2016; slides 11-13.
GB Search Report; dated Jan. 17, 2017; 4 pages.
GB Search Report; dated Oct. 12, 2017; 4 pages.

* cited by examiner

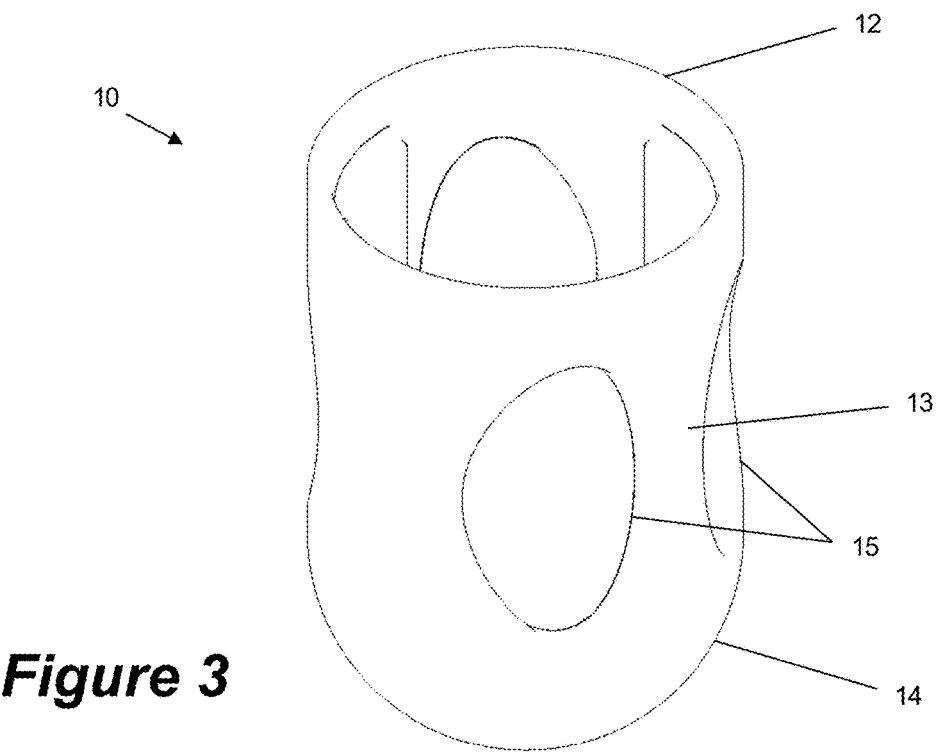
Figure 3
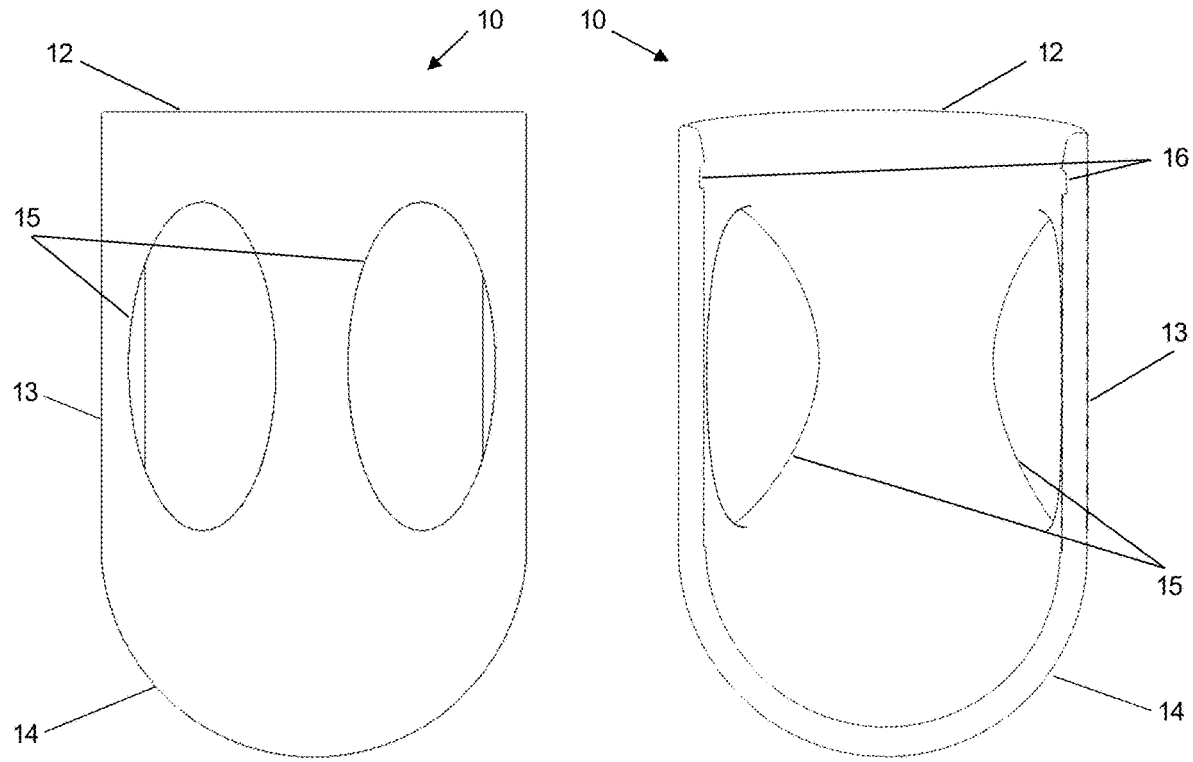
Figure 4  Figure 5

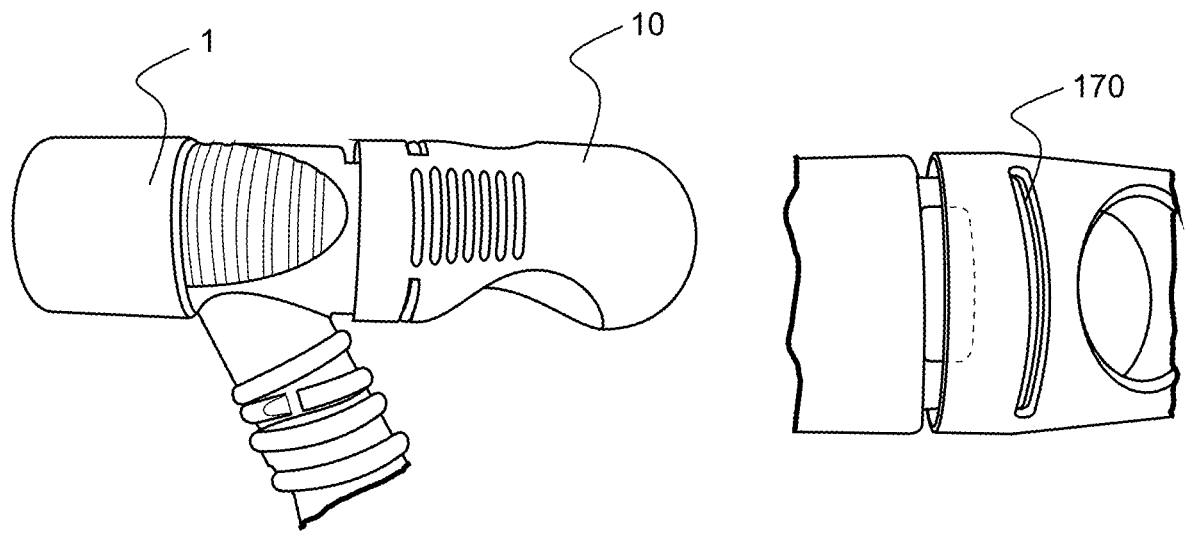
*Figure 17A*    *Figure 17B*
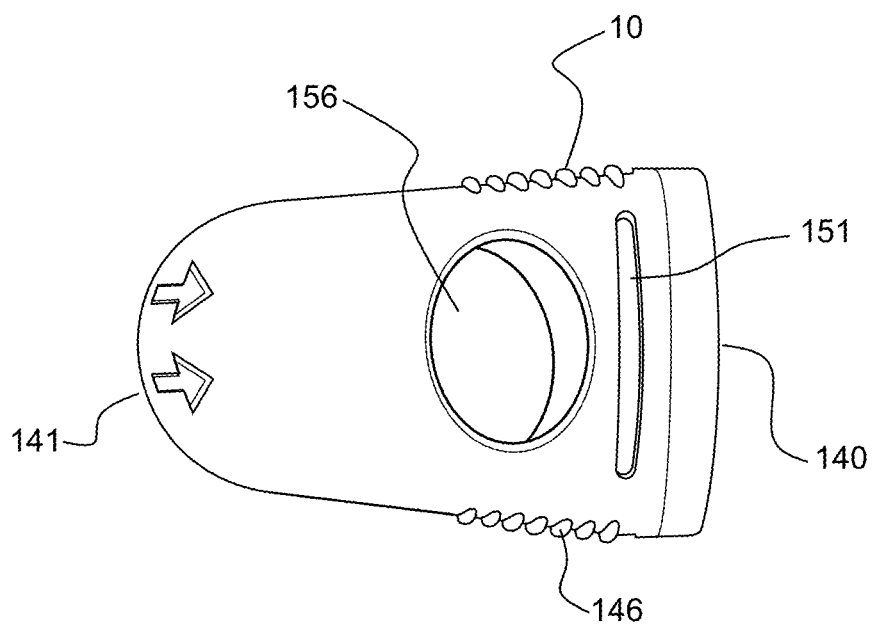
*Figure 18*

TRACHEOSTOMY GUARD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to respiratory assistance systems. More particularly, the present disclosure relates to accessories for invasive ventilation.

Description of the Related Art

Tracheal intubation can be used as part of an invasive respiratory assistance system to deliver gases to a patient. A caregiver inserts a tracheal tube into the airway of a patient, thus, bypassing at least some of the natural humidification process of the body. Gases delivered to the patient can be conditioned prior to delivery, for example, using a humidifier to heat and humidify the gases. A patient interface couples the tracheal tube to a gases delivery conduit to facilitate ventilation.

A tracheostomy guard is coupled to the patient interface to prevent occlusion of the patient interface, for example, by the chin of a patient, bedding or dressings. The tracheostomy guard comprises openings to allow air exchange therein.

Tracheostomy guards can be coupled to the patient interface using a friction fit, or U-shaped clipping mechanism. Such mechanisms have been found to be flimsy and unreliable in use, causing accidental disconnection of the tracheostomy guard in use.

BRIEF SUMMARY

It is an object of the disclosure herein to provide a tracheostomy guard that overcomes or at least ameliorates one or more disadvantages of the prior art, and/or which will at least, provide the public or the medical profession with a useful choice.

Described herein is a tracheostomy guard for a patient interface comprising: a body with a first end with an opening for coupling to or communicating with a patient interface and a second closed end.

Optionally the body is frustoconical or cylindrical.

Optionally the first end is integral with a patient interface.

Optionally the second end is integrally formed with the body.

Optionally the second end is rounded, such as hemispherical.

Optionally the body comprises at least one opening for draining secretions.

Optionally the body comprises two, three or four openings between the first and second ends for draining secretions.

Optionally the openings are elliptical, circular or otherwise shaped.

Optionally the second closed end is configured to deflect secretions towards at least one opening in the body.

Optionally the ribs extend axially long an internal surface of the body.

Described herein is a tracheostomy guard for a patient interface comprising: a body with a first end with an opening for coupling to or communicating with a patient interface and a second closed end.

Optionally the body is frustoconical or cylindrical.

Optionally the second end is rounded, such as hemispherical.

Optionally the second closed end has a diameter that is smaller than at least one axis of the first open end.

Optionally the body tapers from the first open end to the second closed end.

Optionally the body comprises two openings between the first and second ends for draining waste.

Optionally one of the openings is larger than the other opening(s).

Optionally when assembled on a patient interface in use on a patient, the larger opening faces toward the patient.

Optionally each opening may be elliptical, circular or otherwise shaped.

Optionally each opening is a different shape to the other opening(s).

Optionally the tracheostomy guard further comprises an annular portion between the first and second ends.

Optionally the tracheostomy guard further comprises an indicator for guiding assembly with the patient interface.

Optionally the indicator comprises one or more arrows that guide positioning of the two openings upon assembly.

Described herein is a tracheostomy guard for a patient interface comprising: a body with a first end with an opening and a second end, wherein the first end opening is biased into a first configuration, and on application of a force the first end opening can be manipulated into a second configuration, and wherein, in the second configuration, the first end opening is shaped to facilitate coupling a port of a patient interface, and once coupled and after release of the force, the first end opening biases into or at least towards the first configuration which is shaped to engage the port to retain the tracheostomy guard on the patient interface.

Optionally the tracheostomy guard is or comprises a flexible or resilient material to allow movement between the first and second configuration.

Optionally in the first configuration, the first end opening is elongate.

Optionally the first end opening comprises an elliptical or oval shape in the first configuration.

Optionally in the first configuration, the first end opening is substantially oval, with a major axis and a minor axis.

Optionally, upon application of an inward force, the major axis decreases and the minor axis increases in length to manipulate the first end opening into the second configuration.

Optionally, in use, the application of the force is to the major axis of the first end opening.

Optionally the tracheostomy guard further comprises a gripping surface indicating to the user to apply an inward force to the tracheostomy guard at this point.

Optionally the gripping surface comprises a protrusion, roughened surface, or contour.

Optionally the tracheostomy guard further comprises ribs extend axially long an internal surface of the body.

Described herein is a tracheostomy guard for a patient interface comprising: a body with a first end with an opening and a second end, wherein the first end opening is biased into a first configuration, and on application of a force the first end opening can be manipulated into a second configuration, and wherein, in the second configuration, the first end opening is shaped to facilitate coupling a port of a patient interface, and once coupled and after release of the force, the first end opening biases into or at least towards the first configuration which is shaped to retain the tracheostomy guard on the patient interface.

Optionally in the first configuration, the first end opening is elongated.

Optionally in the first configuration, the first end opening is oval, with a major axis and a minor axis, configured such that upon application of the force the major axis decreases and minor axis increases in length to manipulate the first end opening into the second configuration.

Optionally, in use, the application of the force is to the major axis of the first end opening, or alternatively to the body in line with the major axis of the first end.

Optionally, in the second configuration, the first end opening is circular or near circular.

Optionally the body comprises one or more slots, preferably at or near the first end opening.

Optionally first end opening comprises a rim approximately 0.5 mm to 7 mm thick and preferably approximately 1 to 1.8 mm thick.

Optionally the tracheostomy guard further comprises one or more internal stops.

Optionally the tracheostomy guard further comprises one or more support structures.

Optionally the tracheostomy guard further comprises one or more ribs to provide one or more internal stops and/or to provide the one or more support structures.

Optionally the application of the force is to a force application region and the force application region is or has a grip.

Optionally the grip comprises one or more ribs, roughened surfaces, or other detailing to indicate the region, and/or assist with gripping.

Described herein is a tracheostomy guard as described above coupled to a patient interface.

Optionally the patient interface is or comprises a tracheal interface.

Optionally the patient interface comprises a port for coupling with a first end of a tube.

Optionally the assembly further comprises a tube for delivery of gases to the patient interface.

Optionally the tube is permeable to water vapour.

Optionally the tube is impermeable to liquid water or bulk flow of gases.

Optionally a first end of the patient interface is configured or configurable to fluidly connect with the airway of a patient.

Optionally a second end of the patient interface is configured or configurable to couple with the tracheostomy guard.

Optionally the patient interface comprises a vent

Optionally the tracheostomy guard further comprises a connector for connecting a second end of the tube with a gases delivery conduit.

Described herein is a tracheostomy guard as described above coupled to a patient interface.

Optionally the patient interface is a tracheal interface.

Optionally the patient interface comprises a port for coupling with a tube.

Optionally the assembly further comprises a tube for delivery of gases to the patient interface.

Optionally a first end of the patient interface is configured or configurable to fluidly connect with the airway of a patient.

Optionally a second end of the patient interface is configured or configurable to couple with the tracheostomy guard.

Optionally the patient interface comprises a vent.

Described herein is a tracheostomy guard comprising: a first end, a second end, a body formed between the first and second ends, the body comprising at least one opening therein, wherein the second end is a closed end.

Optionally the closed end is configured to prevent the movement of secretions from a patient beyond the tracheostomy guard.

Optionally the first end is integral to a patient interface.

Optionally the first end is configured to couple with a patient interface.

Optionally a portion of the body near the second end is at least partially closed.

Optionally the shape of at least one opening is one of circular, elliptical or substantially triangular.

Described herein is a tracheostomy guard comprising: a first end, a coupling mechanism configured to fluidly connect the first end with a patient interface, a second closed end, a body formed between the first and second ends, the body comprising at least one opening therein, at least one rib extending from the coupling mechanism toward the second closed end, wherein the at least one rib is configured to prevent over-insertion of the tracheostomy guard onto the patient interface.

Optionally the coupling mechanism comprises a releasable snap-fit mechanism.

Optionally the coupling mechanism comprises a groove around an internal perimeter of the first end, and the groove is configured to receive a complementary structure on the patient interface.

Optionally the coupling mechanism is configured to provide a retention force that requires a user to apply a greater force to remove the tracheostomy guard than to insert the tracheostomy guard.

Described herein is a tracheostomy guard comprising: a first end, the first end moveable between a first and a second condition, wherein the first end is biased to the first condition and is configured to grip onto a patient interface.

Optionally a first distance between opposing sides of the first end that is substantially perpendicular to a second distance between opposing sides of the first end, wherein the first distance is larger than the second distance.

Optionally application of a compressive force at or near the opposing sides between which the first distance extends is configured to cause the second distance to increase and thereby move the first end into the second condition.

Optionally the first end comprises an elliptical shape.

Optionally the guard comprises a flexible or resilient material.

Described herein is a tracheostomy guard for a patient interface comprising: a body with a first end with an opening for coupling to a patient interface and a second closed end.

Optionally the body is frustoconical or cylindrical.

Optionally the second closed end is rounded, such as hemispherical.

Optionally the second closed end has a diameter that is smaller that at least one axis of the first open end.

Optionally the body tapers from the first open end to the second closed end.

Optionally the body comprises two openings between the first and second ends for draining waste.

Optionally one of the openings is larger than the other of the openings.

Optionally when assembled on a patient interface in use on a patient, the larger opening faces toward the patient.

Optionally each opening may be elliptical, circular or otherwise shaped, and optionally each opening may be a different shape than the other opening.

Optionally the body comprises additional openings between the first and second ends for draining waste, and preferably at least two additional openings.

Optionally the guard further comprises an annular portion between the first and second ends.

Optionally the guard comprises an indicator on the tracheostomy guard for guiding assembly with the patient interface.

Optionally the indicator comprises one or more arrows that guide positioning of the two openings upon assembly.

Described herein is a tracheostomy guard for a patient interface comprising: a body with a first end with an opening and a second end, wherein the first end opening is biased into a first configuration, and on application of a force the first end opening can be manipulated into a second configuration, and wherein, in the second configuration, the first end opening is shaped to mate a port of a patient interface, and once mated and after release of the force, the first end opening biases into or at least towards the first configuration which is shaped to engage the port to retain the tracheostomy guard on the patient interface.

Optionally in the first configuration, the first end opening is elongated.

Optionally in the first configuration, the first end opening is oval, with a major axis and a minor axis, configured such that upon the application of the force the major axis decreases and the minor axis increases in length to manipulate the first end opening into the second configuration.

Optionally in use the application of the force is to the major axis of the first end opening, or alternatively to the body in line with the major axis of the first end.

Optionally in the second configuration, the first end opening is circular or near circular.

Optionally the body comprises one or more slots, preferably at or near the first end opening.

Optionally the first end opening comprises a rim approximately 0.5 mm to 7 mm thick and preferably approximately 1 to 1.8 mm thick.

Optionally the guard further comprising one or more internal stops.

Optionally the guard comprises one or more support structures.

Optionally the guard comprises one or more ribs to provide one or more internal stops and/or to provide the one or more support structures.

Optionally the application of the force is to a force application region, and the force application region has a grip.

Optionally the grip comprises one or more ribs, roughened surfaces or other detailing to indicate the region and/or assist with gripping.

Optionally the body can have a wall thickness WT of about 0.5 mm to 2 mm, and preferably about 1 mm to about 1.8 mm, and more preferably about 1.4 mm to about 1.5 mm, although these dimensions are only optional. Examples include WT of about 1.25 mm, 1.5 mm or a varying WT of 1.75 mm in some regions and 1.5 mm in other regions.

Described herein is an assembly comprising a tracheostomy guard according to any paragraph above coupled to a patient interface.

In embodiments, a tracheostomy guard is disclosed that comprises a reliable and effective solution to the problems described above. The tracheostomy guard comprises a closed end to deflect patient secretions, and to prevent these from being communicated to a caregiver. Openings within a body of the tracheostomy guard may allow for drainage of secretions to prevent blockage. The openings may provide a space for suctioning the airway therethrough. The tracheostomy guard may have a coupling mechanism that provides a retention force. The retention force may cause a user to apply a greater force to remove than to insert the tracheostomy guard. An embodiment describes at least one rib that may act to prevent over-insertion of the tracheostomy guard, which could lead to occlusion of a vent of the patient interface. An embodiment comprises features to prevent accidental attachment of apparatus to the tracheostomy guard.

Further aspects of the invention, which should be considered in all its novel aspects, will be described in the following description.

It should be noted that various changes and modifications to the presently preferred embodiments described herein will be apparent to those skilled in the art. Such changes and modifications may be made without departing from the spirit and scope of the apparatus and systems of the disclosure and without diminishing its intended advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

Reference to any prior art in this specification is not, and should not be taken as, an acknowledgement or any form of suggestion that that prior art forms part of the common general knowledge in the field of endeavour in any country in the world.

Wherein the foregoing description reference has been made to integers or components having known equivalents thereof, those integers are herein incorporated as if individually set forth.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The apparatus and system of the disclosure may also be said broadly to consist in the parts, elements and features referred to or indicated in the specification of the application, individually or collectively, in any or all combinations of two or more of said parts, elements or features.

BRIEF DESCRIPTION OF THE DRAWINGS

A number of embodiments will now be shown, by way of example, with reference to the following drawings, in which:

FIG. 3 illustrates a perspective view of a tracheostomy guard according to an embodiment of the disclosed apparatus and systems.

FIG. 4 illustrates a front plan view of a tracheostomy guard according to an embodiment of the disclosed apparatus and systems.

FIG. 5 illustrates a front cross-sectional view of a tracheostomy guard according to an embodiment of the disclosed apparatus and systems.

FIG. 17A, 17B illustrates an elevation view of a tracheostomy guard according to an embodiment of the disclosed apparatus and systems connected to a patient interface.

FIG. 18 illustrates an elevation view of a tracheostomy guard according to an embodiment of the disclosed apparatus and systems.

DETAILED DESCRIPTION

During tracheal intubation, patient secretions may be expelled from a patient interface. The secretions may be communicated to a caregiver, for example, through openings in a tracheostomy guard, or directly from the interface. Secretions can exit the openings suddenly and with enough force to reach a caregiver positioned near a patient.

A tracheostomy guard is described that facilitates the removal of secretions therefrom while deflecting secretions such that they are not directed to a caregiver.

Figure 1:
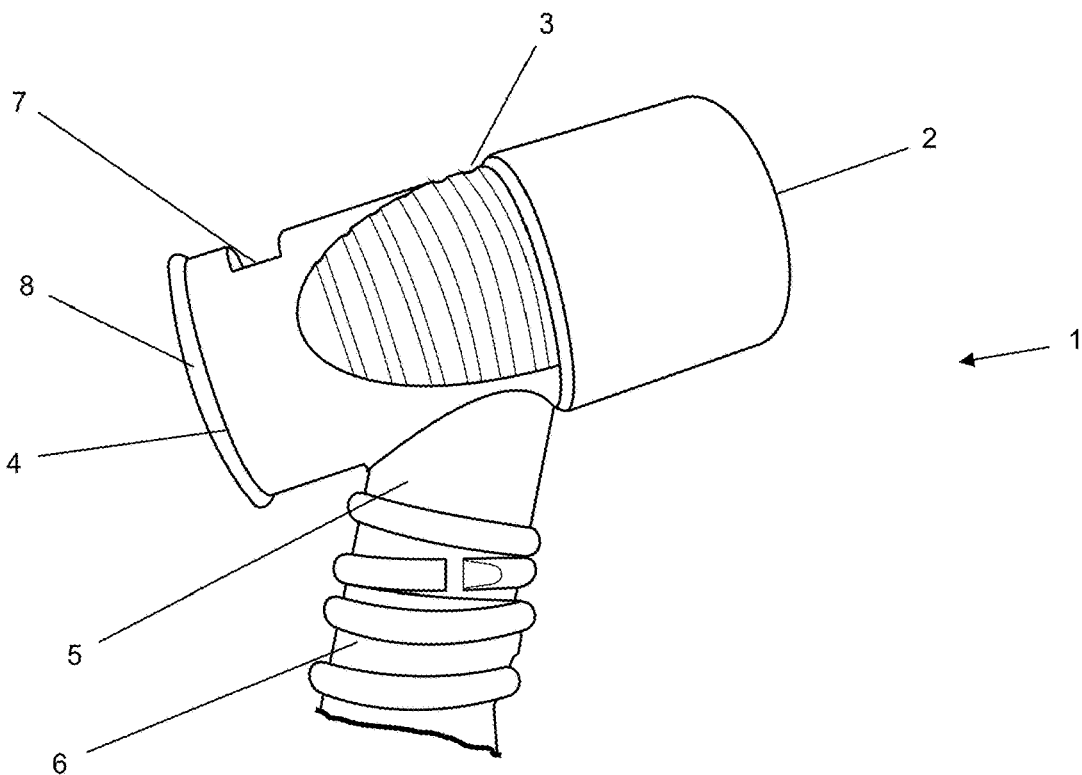
FIG. 1 illustrates a perspective view of a patient interface according to the prior art.
Figure 2:
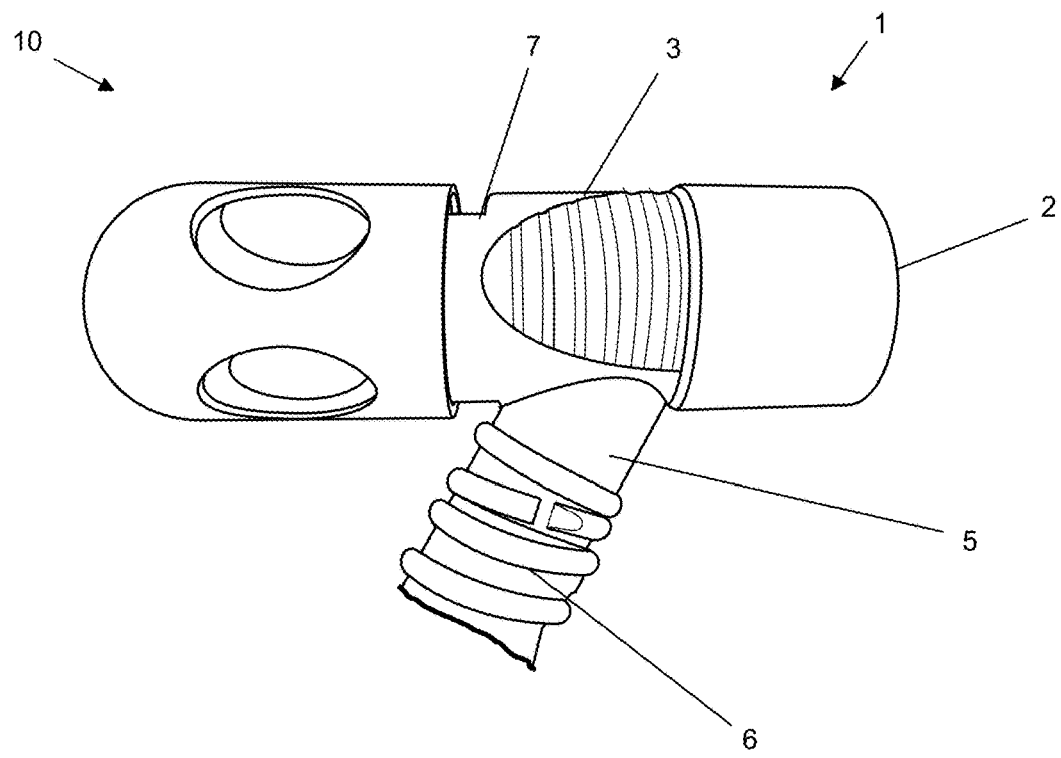
FIG. 2 illustrates a perspective view of a tracheostomy guard according to an embodiment of the disclosed apparatus and systems connected to a patient interface.

FIG. 1 illustrates a patient interface 1, such as a tracheal interface, and FIG. 2 shoes a tracheostomy guard as described herein coupled to a patient interface of FIG. 1. The patient interface 1 is configured to allow respiratory gases to be delivered to a patient. The patient interface 1 comprises a first end 2 and a second end 4 connected by a body 3. The first end 2 of the patient interface is configured to fluidly connect with the airway of a patient. The second end 4 of the patient interface is configured to couple with the tracheostomy guard.

A port 5 couples with a tube 6 which delivers gases to the first end 2 from a gases source (not shown). The first end 2 of the patient interface 1 is configured to fluidly connect with the airway of patient, for example, by coupling with a tracheal tube. The body 3 comprises a vent 7 to prevent accidental occlusion of the patient interface 1, by a patient, caregiver, or due to patient secretions within the patient interface 1. The second end 4 of the patient interface 1 is configured to couple with a tracheostomy guard 10 as shown in FIG. 2.

Referring to FIGS. 3 and 4, an example embodiment of the tracheostomy guard 10 is shown. The tracheostomy guard ("trache guard") 10 comprises a first end or end portion 12 and a second end or end portion 14 with a body 13 therebetween. The first end or end portion 12 is configured to couple with the patient interface 1. The first end or end portion 12 may be integral with the patient interface 1. The first end 12 may comprise a circular cross-section. The first end 12 can comprise any shape that couples with the patient interface 1, and as such, is not limited to a circular cross-section, but could comprise for example, an elliptical, hexagonal, octoganal, or square cross-section. The body 13 is substantially cylindrical in shape. In some embodiments, the body 13 can comprise a substantially cuboidal, frusto-conical or spherical shape. It is to be understood that other suitable shapes are also included within the scope of the disclosure. In the illustrated embodiment, the body 13 is substantially symmetrical along an axial plane. In the embodiment of FIG. 3, the symmetry of the body 13 avoids orientation dependence of the tracheostomy guard 10. As a result, the body 13 can be coupled with the patient interface 1 in any orientation and effectively contain and/or deflect patient secretions in use.

Figure 8:
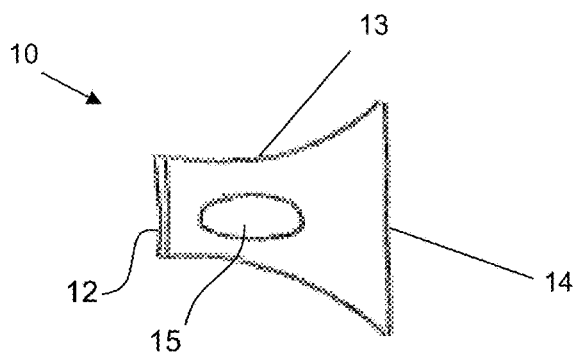
FIGS. 8-10 illustrate front plan views of different embodiments of a tracheostomy guard.
Figure 9:
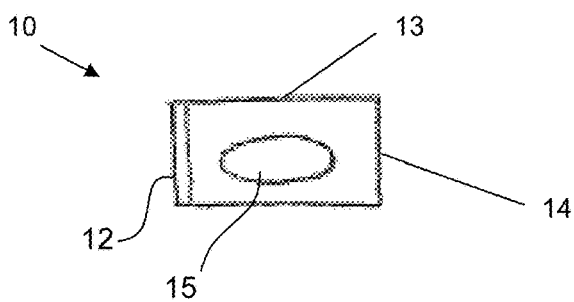
Figure 10:
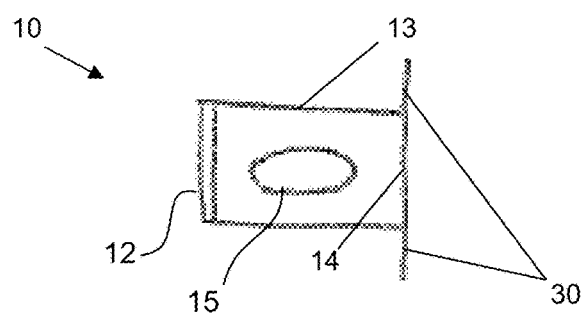

In the illustrated embodiment, the second end 14 comprises a hemispherical shape. As discussed regarding the body 13, the second end 14 can, in some embodiments, form a substantially cuboidal, frustoconical, hexagonal, octagonal, or cylindrical end (see FIGS. 8-10). In some embodiments, the tracheostomy guard 10 can comprise features to prevent incorrect coupling of components thereto. The shape of the second end 14 can discourage a user from incorrectly coupling a component with the tracheostomy guard 10. For example, the shape of the second end 14 can reduce the likelihood that the tracheostomy guard 10 is incorrectly coupled to a ventilator circuit, humidification apparatus, or a gases source, for example, such that occlusion is caused. Referring to FIGS. 8 and 10, the second end 14 can comprise a non-standard medical shape or size, such as a frustoconical end, or member(s) 30 that project beyond the body 13 of the tracheostomy guard 1. In some embodiments, the member(s) 30 project beyond the body 13 in a direction that is substantially offset from, or perpendicular to, an axial axis of the body 13.

The body 13 forms a substantially hollow structure, wherein the first end 12 is open to the atmosphere and able to be in fluid communication with a patient interface 1, and the second end 14 is a closed end. There is a least one annular portion (region) of the body between the first 14 and second ends 12. A "closed end" refers to there being a complete barrier over the end of the body (such as over the end of the annular portion of the body) that prevents passage of fluid.

The first end 12 is configured to fluidly couple with the patient interface 1. The first end 12 is integrally formed with the body 13. The second end 14 is also integrally formed with the body 13.

The body 13 comprises at least one opening 15. The at least one opening 15 is configured to allow patient secretions to drain from the tracheostomy guard 10 in use. The at least one opening 15 can reduce the risk of occlusion or blockage of the patient interface 1. In the illustrated embodiment, four such openings 15 are present. The four openings 15 have been chosen to maximise the area available for drainage from the tracheostomy guard 10. Patients who are undergoing tracheal ventilation may be partially sedated, and at perceived discomfort from the therapy may attempt to remove or adjust the patient interface 1. Therefore, the at least one opening 15 of the tracheostomy guard 10 can be positioned and/or shaped to protect against such interference, by reducing a patient's accessibility to the patient interface 1. A balance between drainage and reduced patient accessibility has been considered in arriving at the present disclosure.

The at least one opening 15 is configured to provide access for a suction tube, such that a caregiver can apply suction to the patient receiving tracheal ventilation. Therefore the size of the at least one opening 15 should be large enough to accommodate a suction tube. In some embodiments, the openings can comprise contours to aid insertion of a suction tube through the patient interface 1. In some embodiments, the at least one opening 15 may comprise a guidance structure that aids a caregiver in positioning and applying suction to the patient.

The size, shape and quantity of the at least one opening 15 can be altered without departing from the scope of the disclosure. The body may comprise at least two, three, four, or more than four openings 15. By way of a non-limiting example, two or three openings could be provided, each comprising a larger area than those in the illustrated embodiment, or more than four openings 15 could be provided, each comprising a smaller area than those in the illustrated embodiment. Alternatively, openings of a different size and/or shape such as, elliptical, circular, or rectangular, could be incorporated into the body 13.

The tracheostomy guard 10 is configured to prevent patient secretions from being communicated to a caregiver. The closed second end 14 deflects secretions towards one or more of the at least one openings 15 in the body 13, causing them to drain therethrough. In some embodiments, a portion of the body 13 proximate to the second end 14 comprises an extension of the closed portion into the body 13 to cause further deflection of patient secretions away from a caregiver, for example, in multiple axes.

Figure 7:
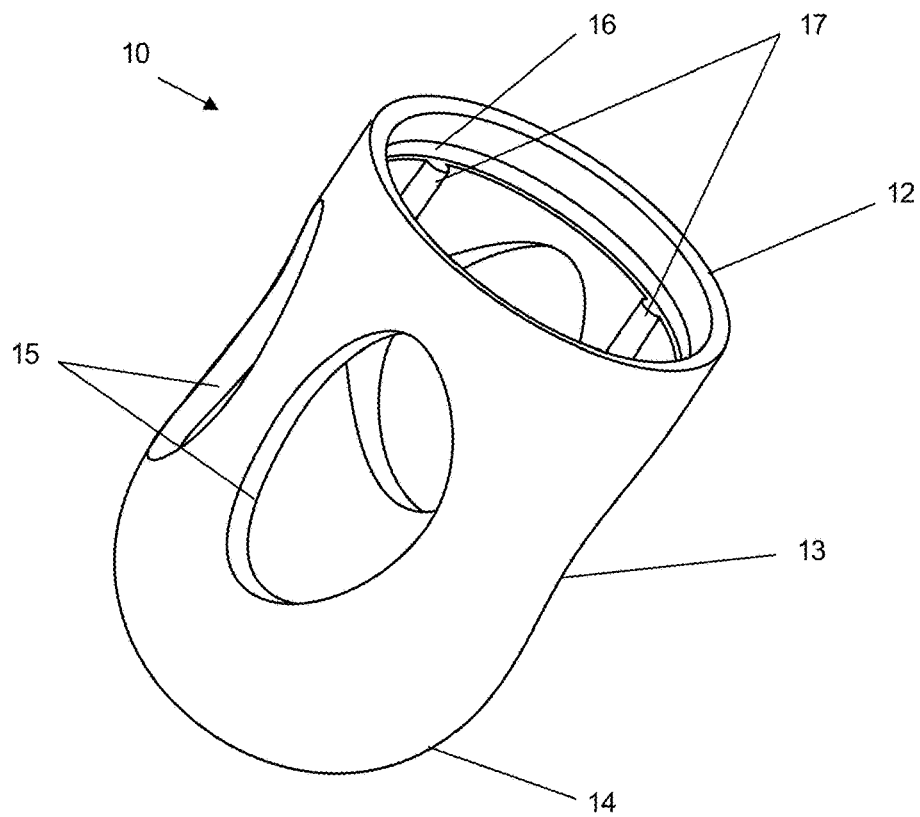
FIG. 7 illustrates a perspective view of a tracheostomy guard according to an embodiment of the disclosed apparatus and systems.

The first end 12 comprises a coupling mechanism 16, as shown more clearly in FIGS. 5 and 7. In the illustrated embodiment, the coupling mechanism 16 comprises a groove about an internal perimeter of the first end 12. The groove is configured to couple with a complementary structure, such as a protrusion 8 shown in FIG. 1. The complementary structure may be located on an outer surface of the patient interface 1. The tracheostomy guard 10 and the patient interface 1 are configured to couple via a snap-fit mechanism. The snap-fit mechanism is configured to releasably couple the tracheostomy guard 10 and the patient interface 1, such that a user can connect and/or disconnect the tracheostomy guard 10 from the patient interface 1. This can be by way of push-fit and/or pull release, whereby the shape of the guard is circular or otherwise similar in shape to the patient interface so it can couple snugly thereto. A user may temporarily disconnect the tracheostomy guard 10, for example, for cleaning, or to better access the patient interface 1.

The coupling mechanism 16 is configured to facilitate coupling between the patient interface 1 and the tracheostomy guard 10, with a sufficient retention force to reduce the likelihood of accidental disconnection or removal of the tracheostomy guard 10. The force to remove the tracheostomy guard 10 from the patient interface 1 should therefore be greater than forces that are likely to be encountered during use. Minimal force should be required to couple the tracheostomy guard 10 to the patient interface 1 in use to reduce discomfort to a patient. In some embodiments, the force required to decouple the tracheostomy guard 10 from the patient interface 1 is greater than the coupling force.

In the illustrated embodiment and by way of example only, the tracheostomy guard 10 comprises an internal diameter of 17 mm. The groove of the coupling mechanism 16 extends 1 mm into the first end 12. It is to be understood that the tracheostomy guard 10 can be adapted to fit different patient interfaces and/or scaled as appropriate, and therefore such modifications are included within the scope of the disclosure. The size of the tracheostomy guard 10 can be chosen such that it is not obstructive to a patient and/or caregiver, but provides a sufficient barrier to occlusion and/or is able to deflect patient secretions such that they are not communicated with a caregiver.

Figure 12:
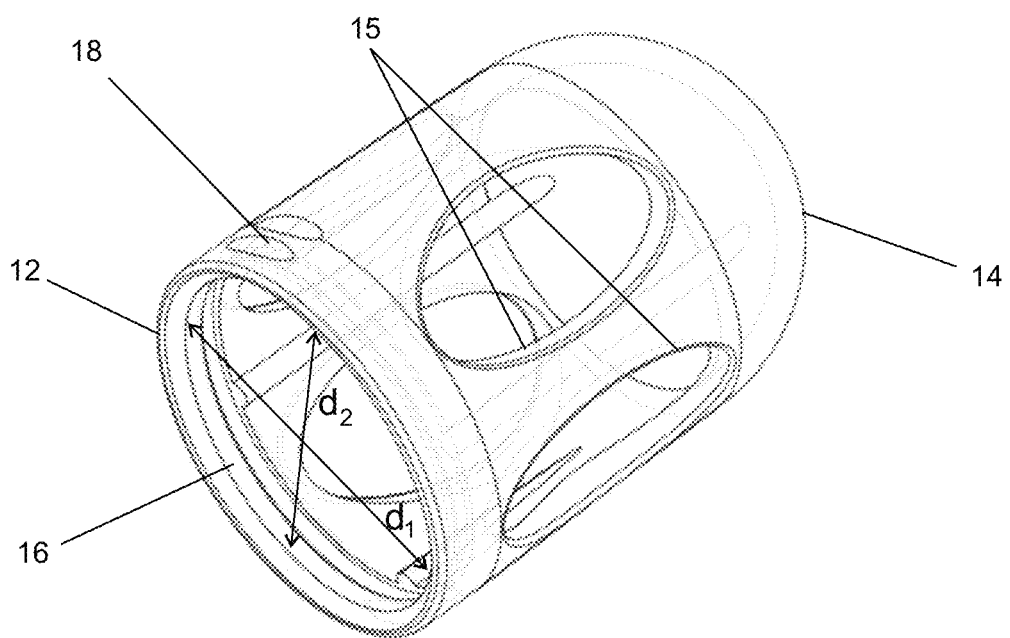
FIG. 12 illustrates a perspective view of a tracheostomy guard according to an embodiment of the disclosed apparatus and systems.
Figure 13A:
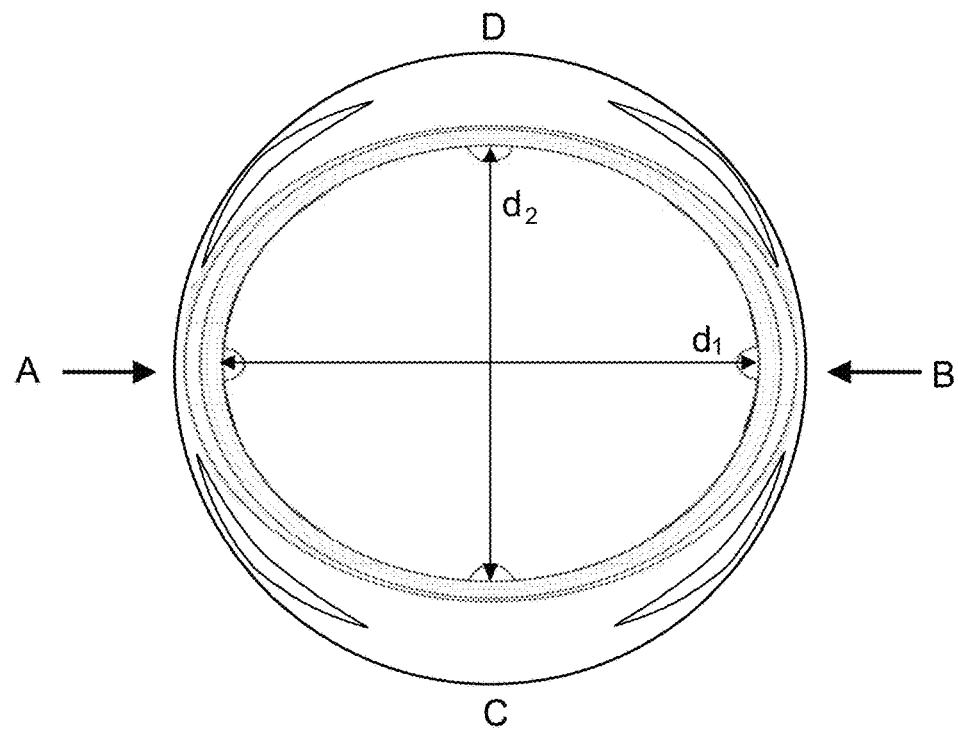
FIGS. 13A and 13B illustrate two views of a tracheostomy guard according to an embodiment of the disclosed apparatus and systems.
Figure 13B:
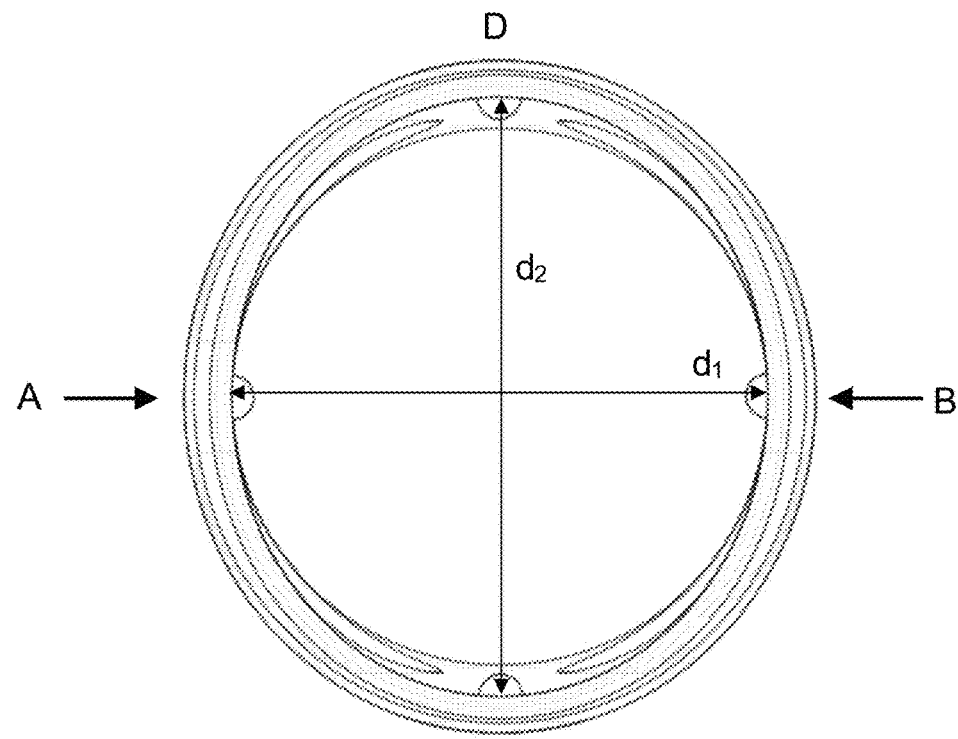

In some embodiments, the first end 12 comprises an elongated or oval shape in a first condition, as shown in FIGS. 12, 13A, 13B. The elongated shape comprises a first internal diameter $d_1$ that is larger than a second internal diameter $d_2$ in the first configuration. In the first configuration, the diameter $d_2$ is the same size as or smaller than the external diameter of the second end 4 of the patient interface 1. In the second configuration, the diameter $d_2$ is larger or approximately the same size as an external diameter of the second end 4 of the patient interface 1. For example, the diameter $d_2$ may be larger than, slightly larger than, the same size as, or slightly smaller than the diameter of the second end 4 in the second configuration. The tracheostomy guard 10 comprises a flexible or resilient material to allow movement between the first condition and a second condition.

To move to the second condition, an inward force can be applied to points A and B causing them to move towards each other, decreasing the diameter $d_1$. This causes points C and D to move apart, increasing the diameter $d_2$. The increased diameter $d_2$ facilitates coupling of the tracheostomy guard 10 with the patient interface 1. Once the tracheostomy guard 10 has been fitted onto the patient interface 1, over the protrusion 8, the force is removed allowing the diameter $d_1$ and the diameter $d_2$ to return to the first condition. The diameter $d_2$ thus grips onto the patient interface 1. To remove the tracheostomy guard 10, a force is applied to points A and B, causing the diameter $d_2$ to increase in size, allowing the tracheostomy guard 10 to be removed from the patient interface 1. This mechanism of coupling the tracheostomy guard 10 to the patient interface 1 allows force to be applied in a plane that reduces the discomfort to a patient. For example, forces are applied substantially perpendicular to the axis of connection between the tracheostomy guard 10 and the patient interface, which reduces the impact of these forces on the patient because the force is not applied in a direction towards the patient.

In some embodiments, at least one gripping surface 18 indicates to the user to apply an inward force to the tracheostomy guard 10 at this point. In the illustrated embodiment, the gripping surface 18 comprises at least one recess at the first end 12. In some embodiments, the gripping surface 18 can comprise at least one protrusion, roughened surface or contour, to encourage a user to grip the tracheostomy guard 10 at the first end 12. In some embodiments, visual indicators, such as colour, or communication via a message or pictorial form could encourage a user to grip the tracheostomy guard 10 at the first end 12.

Materials can be chosen that are robust enough to withstand repeated connection and/or disconnection of the tracheostomy guard 10 to the patient interface 1. In an embodiment, the tracheostomy guard 10 comprises a thermoplastic polymer, such as polypropylene.

In some embodiments, a clipping mechanism (not shown) can couple and/or decouple the tracheostomy guard 10 to the patient interface 1. The clipping mechanism can reduce the forces that are required due to a snap-fit or friction fit mechanism, which may improve patient comfort. The clipping mechanism can be activated once the tracheostomy guard 10 is positioned near the patient interface 1, such that coupling and/or decoupling can occur. The clipping mechanism may improve patient comfort during coupling and/or decoupling of the tracheostomy guard 10.

Figure 6:
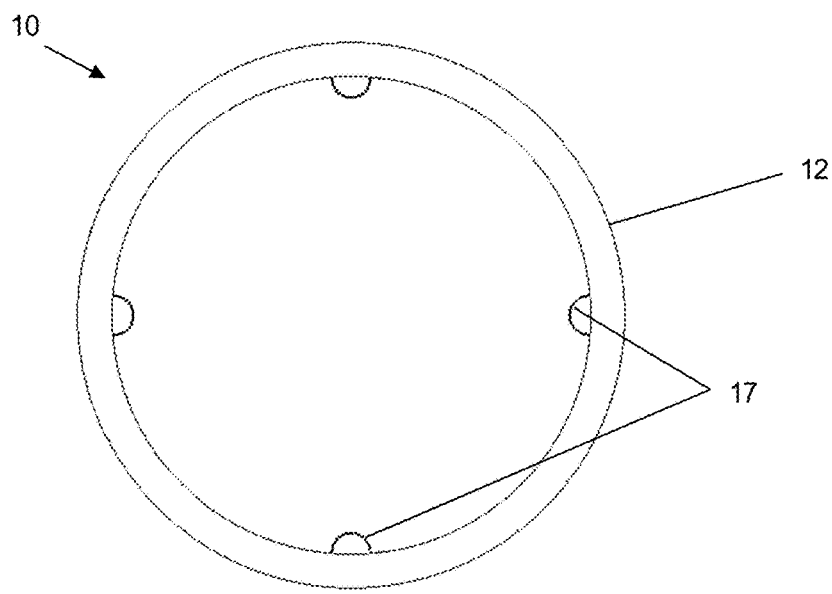
FIG. 6 illustrates a top plan view of a tracheostomy guard according to an embodiment of the disclosed apparatus and systems.

In some embodiments, and as illustrated in FIGS. 6 and 7, the tracheostomy guard 10 comprises ribs 17. The ribs 17 extend axially along an internal surface of the body 13. The ribs 17 abut an edge of the coupling mechanism 16 of the tracheostomy guard 10. The ribs 17 act as a stop to prevent over-insertion of the patient interface 1 into the tracheostomy guard 10 during connection. In some embodiments, the patient interface 1 comprises a vent 7 that is configured to provide venting of respiratory gases should occlusion of the opening at the first end 12 occur (see FIGS. 1 and 2). The ribs 17 act to prevent the tracheostomy guard 10 from occluding the vent. In some embodiments, the ribs 17 may also provide structural support to the tracheostomy guard 10. In the illustrated embodiment, the tracheostomy guard 10 receives the patient interface 1 to form a connection therebetween. It is to be understood that in some embodiments, the tracheostomy guard 10 is received by the patient interface 1 and comprises at least some of the described features.

In the illustrated embodiment, four ribs 17 are provided. It is to be understood that multiple ribs 17, for example, two or three ribs, may be provided without departing from the scope of the disclosure. The ribs 17 may be substantially evenly spread about the perimeter of the internal surface of the body 13. In the illustrated embodiment, one of the ribs 17 is positioned between each pair of the openings 15. Spacing of the ribs 17 helps to reduce any torsional effects that may occur during connection and that could lead to occlusion of the vent 7. In some embodiments, material choice can mitigate the risk of torsional effects, and therefore the spacing of the ribs 17 can be adjusted without causing occlusion of the vent 7. Alternatively, a single rib 17 can act as a stop to prevent over-insertion of the patient interface 1 during connection.

Figure 11:
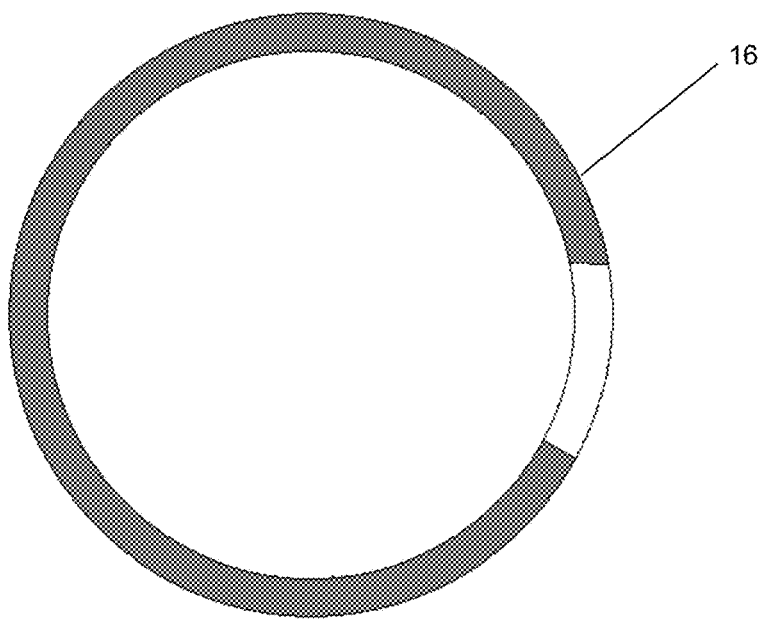
FIG. 11 illustrates a top plan view of a tracheostomy guard according to an embodiment of the disclosed apparatus and systems.

In some embodiments, the coupling mechanism 16 comprises a clip as shown in FIG. 11. The clip is formed at least partially about the perimeter of the first end 12 and can comprise a shape, for example, such as a horseshoe. The clip couples with a complementary structure such as a protrusion or wedge. Clipping between the tracheostomy guard 10 and the patient interface 1 can occur due to deformation that occurs at the clip, which allows it to stretch over the complementary structure before gripping the patient interface 1. Material choice can provide a clip that is robust and can maintain a firm hold on the patient interface 1 to prevent accidental removal of the tracheostomy guard 10 in use. In some embodiments, the clip can be in combination with features described in the disclosure, for example, the ribs 17, to prevent the risk of over-insertion of the patient interface 1 to the tracheostomy guard 10.

In some embodiments, the coupling mechanism 16 comprises a squeezable mechanism to facilitate coupling between the patient interface 1 and the tracheostomy guard 10. Force applied by a user to the squeezable mechanism causes the perimeter of the first end 12 to expand, facilitating coupling therebetween. Removal of the applied force causes the perimeter of the first end 12 to return to its original size. The squeezable mechanism may reduce the forces applied to the neck of the patient during connection and/or disconnection of the tracheostomy guard 10 to the patient interface 1. This may result in increased patient comfort.

The tracheostomy guard 10 may be a disposable component. In some embodiments, aesthetic features of the tracheostomy guard 10 can encourage disposal of the component following use. Colour can be used to indicate that the tracheostomy guard 10 is a disposable component. For example, blue can indicate to the user that they should dispose of the tracheostomy guard 10 following use. Other colours for example, red or yellow, could also be used. In the illustrated embodiment, the tracheostomy guard 10 comprises an opaque material. In some embodiments, a translucent or transparent material can be used to indicate to the user that the tracheostomy guard 10 is a disposable component. In some embodiments, the tracheostomy guard 10 may comprise a surface on an outer surface of the body 13, or, at or near the second end 14 that can communicate with a user to dispose of the component. Communication can be in the form of a message, such as written instructions, or in pictorial form.

Referring to FIGS. 14 to 20, another example embodiment of the tracheostomy guard 10 is shown. This operates and engages with the patient interface 1 (such as tracheal/patient interface) in a similar manner to the previous embodiment, but has some different or additional features, which are described in detail below.

Figure 14:
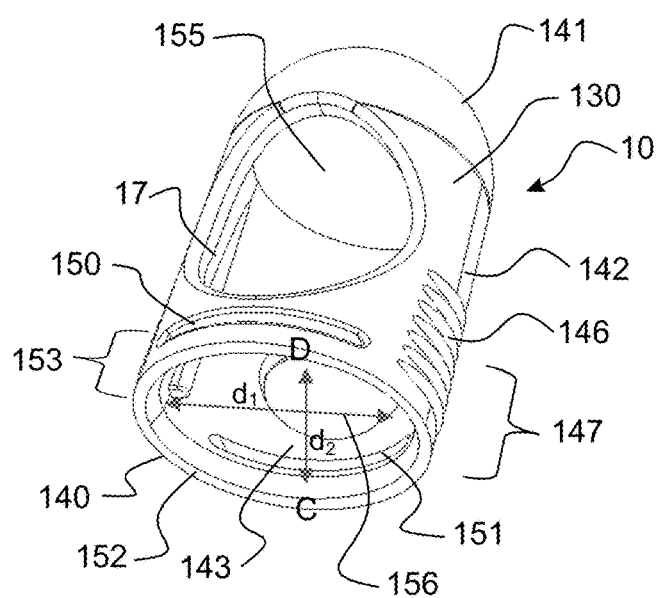
FIG. 14 illustrates a perspective view of the tracheostomy guard according to an embodiment of the disclosed apparatus and systems.
Figure 19:
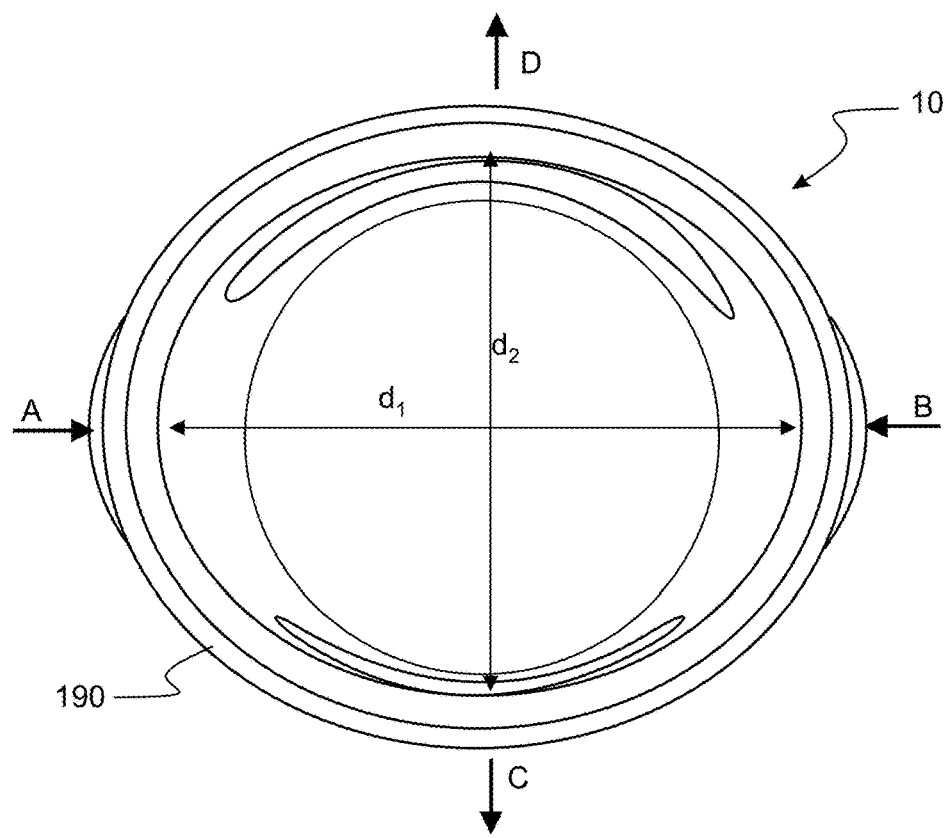
FIGS. 19 and 20 illustrate a plan view of a tracheostomy guard in first and second configurations respectively according to an embodiment of the disclosed apparatus and systems.

The tracheostomy guard 10 has a body 142 that comprises a first end 140 and a second end 141. There is a least one annular portion (region) of the body between the first 14 and second ends 12. The body can have a wall thickness WT (See FIG. 15B) of about 0.5 mm to 2 mm, and preferably about 1 mm to about 1.8 mm, and more preferably about 1.4 mm to about 1.5 mm, although these dimensions are only optional. Examples include wall thicknesses of about 1.25 mm, 1.5 mm or a varying WT of 1.75 mm in some regions and 1.5 mm in other regions. The first end 140 is configured or configurable to be coupled with the patient interface 1. The first end 140 comprises an opening 143 which can take different configurations (conditions). The first end 140 is formed in one end of the body 142, which is fabricated from a flexible and/or resilient plastics material. The first end opening 143 is normally biased into a first configuration 190 (first condition) with an elongated (such as elliptical/oval) cross-sectional shape (see e.g. FIGS. 14 and 19). The elongated shape has a major and minor axis—the major axis being longer than the minor axis. The flexible and/or resilient nature of the plastics body 142 and shape biases the first end opening 143 into this first configuration. FIGS. 14 and 19 show the first end opening in its normally biased first configuration according to one possible shape.

In the illustrated example, the elongated shape comprises a first internal diameter (major axis) $d_1$ that is larger than a second internal diameter (minor axis) $d_2$. In the first configuration, the diameter $d_2$ is the same size as or smaller than the external diameter of the second end 4 of the patient interface 1. In the second configuration, the diameter $d_2$ is approximately the same size as an external diameter of the second end 4 of the patient interface 1. For example, the diameter $d_2$ may be slightly larger than, the same size as, or slightly smaller than the diameter of the second end 4 in the second configuration.

Figure 16:
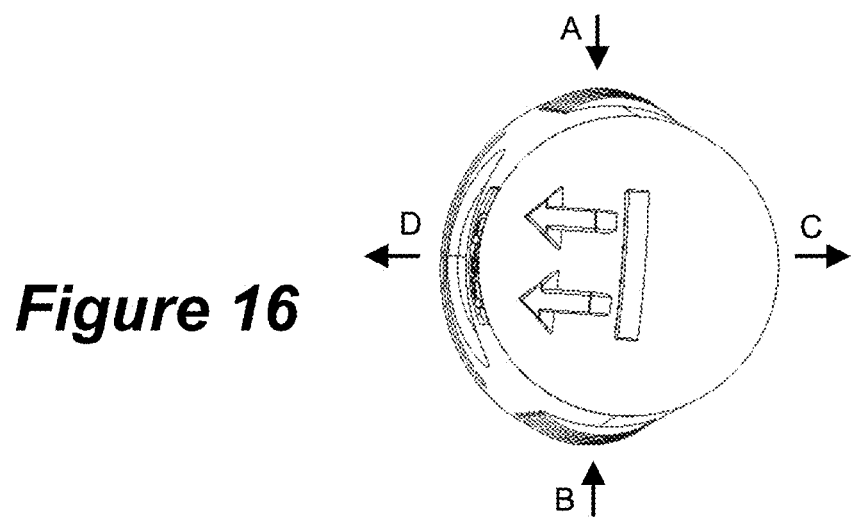
FIG. 16 illustrates a top plan view of a tracheostomy guard according to an embodiment of the disclosed apparatus and systems.
Figure 20:
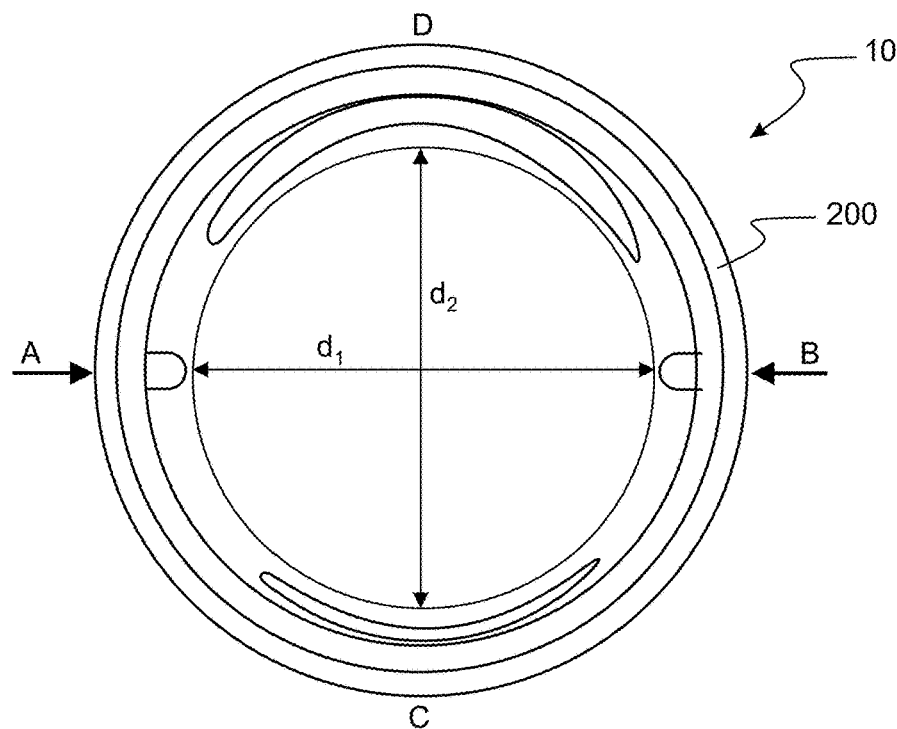

The tracheostomy guard 10 body 142 comprises a flexible and/or resilient material to allow movement between the first configuration 190 (first condition)—see FIG. 19; and a second configuration 200 (second condition)—see FIG. 20. With an application of an external force, such as on the side of the body 142 and/or at the side of the first end/opening, the first end opening 143 can be configured/manipulated into the second configuration 200. The external force could be a squeezing force from the fingers/thumb of a user, for example. FIG. 16 indicates with arrows A and B where the force could be applied—this being a force application region. The force is preferably applied at a region at the apexes (opposite ends of the major axis) of the elongated shape. The external force reacts against and overcomes (or at least partially overcomes) the bias force in the body/first end that normally biases the first end opening into the first configuration.

Referring to FIG. 20 in the second configuration 200, the first end opening 143 is shaped such that it can mate/couple/connect with the port/second end 4 of the patient interface 1. This means that the shape and size of the first end opening 143 in the second configuration matches, is similar to, or is otherwise commensurate with the shape and size of the port 4 of the patient interface 1 such that the two can join. For example, the second configuration might be of a shape and/or size that the port 4 can insert into (that is the opening 143 can slide over the port 4), or alternatively of a shape and/or size such that the first end 143 can insert into the port 4 (that is, the port can slide over the opening 143). It is preferred but not essential that opening 143 slides over the port 4 and the remainder of the embodiment will refer to that alternative. In this specification, reference to "shape" of the first and second configurations can be generally used to reference size as well as shape. The shape of the second configuration is preferably a circular or near circular cross-section, but that is preferred only, and not an essential configuration. The shape of the second configuration alternatively could comprise, for example, an elliptical, hexagonal, octagonal, or square cross-section. Upon releasing the external force, the first end opening 143 reverts into the normally biased first configuration, under the resilience of the plastics material of the body 142. Referring to the cross-sectional view in FIG. 15B, the opening 143 has an edge/rim 152. The wall proximate the rim is thinned 153 to provide an internal diameter 158 that is greater than the external diameter of the patient interface port 4, so that in the second configuration the opening can slide over the port 4. The thinned wall transitions into a lead-in chamfer 159, for assisting further insertion of the opening 143 over the port 4 into a mating position to be described later. The rim could be about 0.5 mm to 7 mm thick, or preferably about 1 mm to 1.8 mm thick.

The first end 140 comprises a coupling (coupling region) 147. In the illustrated embodiment, the coupling 147 comprises the rim 152, the thinned wall 153, the chamfer 159, and/or one or more slots 150, 151, preferably at or near the first end opening 143, and preferably about the perimeter 152 of the first end opening 143. The one or more slots 150, 151 extend at least partially around the opening perimeter 152 and are configured to couple with a complementary structure, e.g. one or more corresponding protrusions 170 (see FIG. 17A and close up FIG. 17B), on the patient interface 1. The complementary structure is preferably located on an outer surface of the patient interface 1. For example, the protrusions 170 might be one or more rails, rims or similar, around or near the rim of the port opening 2 as shown in FIGS. 17A, 17B. The engagement of the complementary structure 170 and the slots 150, 151 on the tracheostomy guard 10 assist to retain the tracheostomy guard on the patient interface 1.

In use, when an external force e.g. at force application regions A/B, is applied at the force application regions and the first end 140 is manipulated into the second configuration 200, the shape of the second configuration enables the first end opening 143 to be slid over the port 4 and the complementary structure 170. The thinned wall 153 enables the internal diameter of the opening 143 to go over the port external diameter, and the chamfer 159 assists further sliding of the opening 143 over the complementary structure 170 on the patient interface, so it can locate and engage with the slots 150, 151. Upon releasing the force, the first end opening 143 reverts back to the first configuration 190 under the bias of the resilient/flexible body. Due to the shape of the patient interface, it may not be possible for the first opening 143 to revert fully back to the first configuration, in which case the first opening is biased at least some way towards the first configuration as far as it will go before being prevented by interference with the patient interface shape. The shape and biasing are such that the one or more slots 150, 151 on the tracheostomy guard 10 engage with the complementary structure 170 on the patient interface 1 to retain the guard 10 on the interface. To remove the tracheostomy guard 10, an external force e.g. at force application regions A/B, is applied again at the force application regions such that the first end opening 143 goes into the second configuration 200, the one or more slots 150, 151 disengage from the complementary structure 170, and the guard 10 can be slid off and released from the patient interface 1.

Preferably the coupling portion 147 of the tracheostomy guard (for example, the thinned body wall 153 around the opening of the first end) has all sides of the same thickness. Alternatively, different sides could have different thicknesses e.g. 1.75 mm for two sides and 1.5 mm for two sides, or e.g. three sides could be the same and one different, or all sides could have different thicknesses. If the force application regions A, B where a squeezing force is applied are thinned, this can make the guard easier to squeeze for attachment/detachment. It has been determined that if the gripping side (region) is thicker, the guard is harder to squeeze—even if the other sides (regions) are thinner. The thinner force application regions A/B make it easy to squeeze such that a reduced force is required to be applied to the patient when coupling the guard and interface. Similarly, the squeezing mechanism allows the force to be applied in a direction that is perpendicular to the direction of insertion to reduce the forces applied directly to the patient. The wall thickness can be designed such that the guard 10 is easily squeezed and thus detached, yet is less likely to fall off. To make the guard 10 harder to squeeze (as the removal force should not be so low that it will fall off) the region where a squeezing force is applied can be thicker relative to the deforming regions. That is, the wall thickness and material will be chosen or designed such that the tracheostomy guard is easy to squeeze to be removed but also rigid or stiff enough such that the tracheostomy guard will not be accidentally removed if a relatively small force is applied or the guard is accidentally knocked.

As an example, to move to the second configuration 200, an inward force can be applied to points A and B (see FIG. 16) reacting against the biasing force of the flexible and/or resilient plastics body causing them to move towards each other, decreasing the diameter $d_1$. This causes points C and D to move apart (from first configuration in FIGS. 14/19 to second configuration in FIG. 20), increasing the diameter $d_2$. The increased diameter $d_2$ facilitates coupling of the tracheostomy guard 10 with the patient interface 1. Once the tracheostomy guard 10 has been fitted onto the patient interface 1 port 4, over the protrusions 170, the force is removed allowing the diameter $d_1$ and the diameter $d_2$ to return to the first configuration 190. The diameter $d_2$ reduces so that the slots 150, 151 engage onto the rails 170 of the patient interface 1. To remove the tracheostomy guard 10, a force is applied to points A and B, causing the diameter $d_2$ to increase in size, allowing the tracheostomy guard 10 to be removed from the patient interface 1. This mechanism of coupling the tracheostomy guard 10 to the patient interface 1 allows force to be applied in a plane that reduces the discomfort to a patient. For example, forces are applied substantially perpendicular to the axis of connection between the tracheostomy guard 10 and the patient interface 1, which reduces the impact of these forces on the patient because the force is not applied in a direction towards the patient.

In some embodiments, at least one gripping surface 146 (preferably on, near, at or around the force application region/points A, B) indicates to the user to apply an inward force to the tracheostomy guard 10 at this point. In the illustrated embodiment, the gripping surface 146 comprises one or more ribs at and/or towards the first end 140, and/or on the body 142, at the apexes of the major axis. In some embodiments, the gripping surface 146 can comprise at least one protrusion, roughened surface or contour, to encourage a user to grip the tracheostomy guard 10 at the first end 12. In some embodiments, visual indicators, such as colour, or communication via a message or pictorial form could encourage a user to grip the tracheostomy guard 10 at the first end 140.

The coupling 147 is configured to facilitate coupling between the patient interface 1 and the tracheostomy guard 10, with a sufficient retention force to reduce the likelihood of accidental disconnection or removal of the tracheostomy guard 10. The force to remove the tracheostomy guard 10 from the patient interface 1 (without external force to put the first end opening 143 into the second configuration) should therefore be greater than forces that are likely to be encountered during use. That is, the bias force in the first configuration engages the slots to the rails with sufficient force to prevent or at least restrict disengagement of the slots/rims under normal use (e.g. through axially pulling of the guard relative to the port), without applying the external force at the force application regions. Using the external force to change the shape of the first end opening 143, reduces the force required to remove the tracheostomy guard from the patient interface.

This embodiment, the guard 10 can have similar dimensions to the previous embodiment. It is to be understood that the tracheostomy guard 10 can be adapted to fit different patient interfaces and/or scaled as appropriate, and therefore such modifications are included within the scope of the disclosure. The size of the tracheostomy guard 10 can be chosen such that it is not obstructive to a patient and/or caregiver, but provides a sufficient barrier to occlusion and/or is able to deflect patient secretions such that they are not communicated with a caregiver.

Materials can be chosen that are robust enough to withstand repeated connection and/or disconnection of the tracheostomy guard 10 to the patient interface 1. In an embodiment, the tracheostomy guard 10 comprises a thermoplastic polymer, such as polypropylene.

Figure 15A:
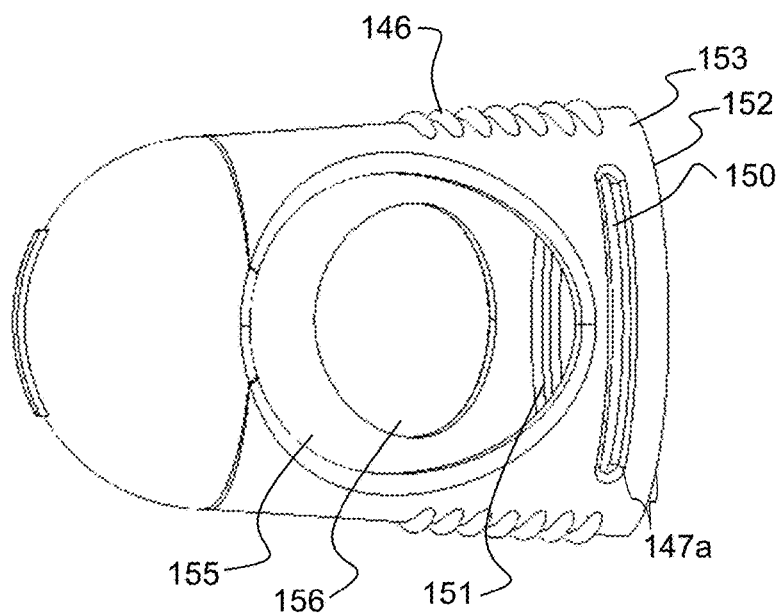
FIGS. 15A and 15B illustrate an elevation (full and cross-sectional) view of a tracheostomy guard according to an embodiment of the disclosed apparatus and systems.
Figure 15B:
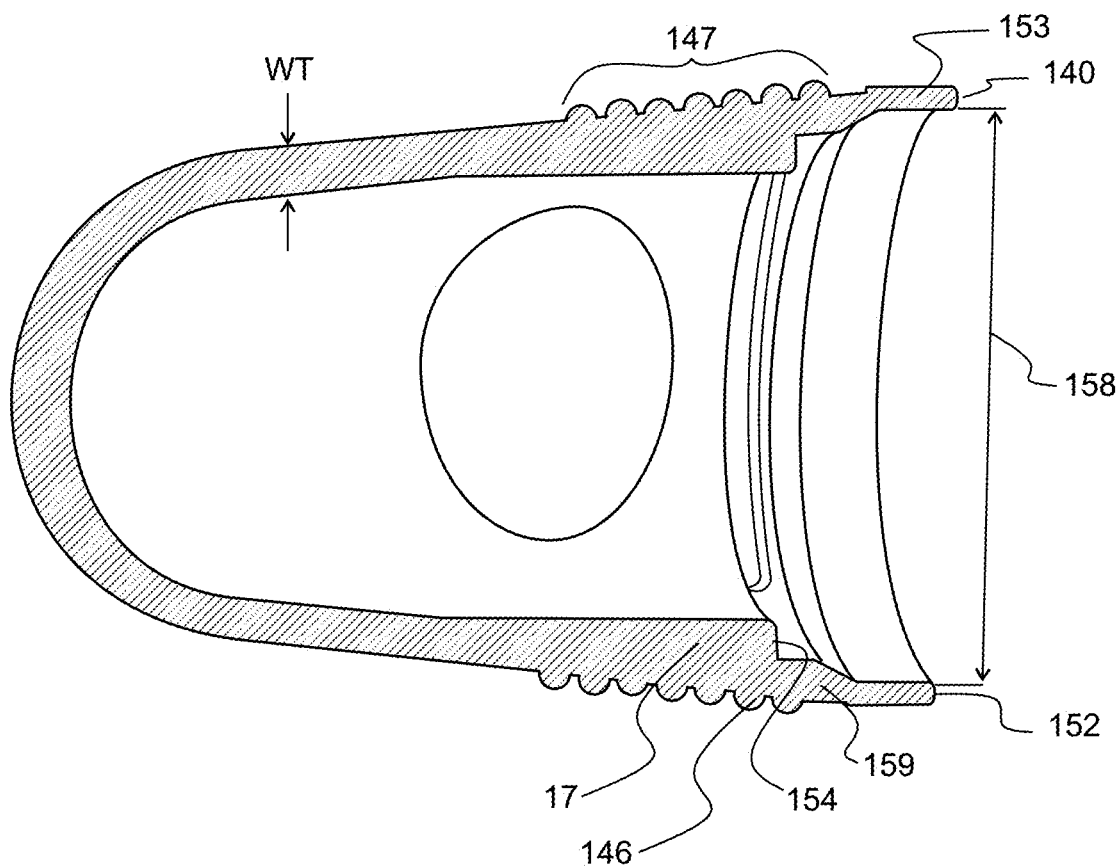

Preferably, the tracheostomy guard 10 comprises one or more stops 154—see FIG. 15B to prevent over-insertion of the guard 10 onto the interface 1. The stops 154 could be formed from the end of ribs 17. The ribs 17 extend axially along an internal surface of the body 142. The ribs 17 abut an edge of the coupling mechanism 16 of the tracheostomy guard 10. The ribs 17 act as a stop to prevent over-insertion of the patient interface 1 into the tracheostomy guard 10 during connection. In some embodiments, the patient interface 1 comprises a vent 7 that is configured to provide venting of respiratory gases should occlusion of the opening at the first end 140 occur. The ribs 17 act to prevent the tracheostomy guard 10 from occluding the vent 7. In some embodiments, the ribs 17 may also provide structural support to the tracheostomy guard 10, for example by providing rigidity. In the illustrated embodiment, the tracheostomy guard 10 receives the patient interface 1 to form a connection therebetween. It is to be understood that in some embodiments, the tracheostomy guard 10 is received by the patient interface 1 and comprises at least some of the described features.

In the illustrated embodiment, two ribs 17 are provided. It is to be understood that multiple ribs 17, for example, two or three ribs, may be provided without departing from the scope of the disclosure. The ribs 17 may be substantially evenly spread about the internal surface of the body 142. In the illustrated embodiment, the ribs 17 are positioned between the openings 155, 156. Spacing of the ribs 17 helps to reduce any torsional effects that may occur during connection and that could lead to occlusion of the vent 7. In some embodiments, material choice can mitigate the risk of torsional effects, and therefore the spacing of the ribs 17 can be adjusted without causing occlusion of the vent 7. Alternatively, a single rib 7 can act as a stop to prevent over-insertion of the patient interface 1 during connection. There may also be no ribs.

The body 142 extends between the first 140 and second 141 ends and is preferably partially or substantially cylindrical or frustoconical in shape. In some embodiments, the body 142 can alternatively comprise a partially or substantially cuboidal or spherical shape. Other shapes are possible. It is to be understood that other suitable shapes are also included within the scope of the disclosure. In the illustrated embodiment, the body 142 is substantially symmetrical along an axial plane. The symmetry of the body 142 avoids orientation dependence of the tracheostomy guard 10. As a result, the body 142 can be coupled with the patient interface 1 in any orientation and effectively contain and/or deflect patient secretions in use, although there is a preferred orientation of connection, which will be described later. The length of the tracheostomy guard 10 is designed so that when the tracheostomy guard 10 is coupled with the tracheal interface 1, it will not occlude slots on the interface 1. That is, the (thin wall) portion 153 of the coupling region 147 that lies between the slots 150 of the tracheostomy guard and the first end/edge/rim 152 of the tracheostomy guard 10 is sufficiently long to extend up to the vent slot 7 of the interface 1 to allow for deflection without breakage, but not so long that it will block the vent slots 7 on the interface 1. The length is chosen (slightly covering the vent slot 7) as it reduces secretions splashing out of the vent slot 7 without obscuring the vent slot 7. The coupling region provides a lead-in for the tracheostomy guard 10 over the interface 1 opening.

In the illustrated embodiment, the second end 141 comprises a hemispherical shape. As discussed regarding the body 142, the second end 141 can, in some embodiments, form a substantially cuboidal, frustoconical, hexagonal, octagonal, or cylindrical end. In a variation, as shown in FIG. 18, the second end is tapered. In some embodiments, the tracheostomy guard 10 can comprise features to prevent incorrect coupling of components thereto. The shape of the second end 14 can discourage a user from incorrectly coupling a component with the tracheostomy guard 10. For example, the shape of the second end 14 can reduce the likelihood that the tracheostomy guard 10 is incorrectly coupled to a ventilator circuit, humidification apparatus, or a gases source, for example, such that occlusion is caused. The second end 141 can comprise a non-standard medical shape or size, such as a frustoconical end, or member(s) that project beyond the body 142 of the tracheostomy guard 1. In some embodiments, the member(s) project beyond the body 142 in a direction that is substantially offset from, or perpendicular to, an axial axis of the body 142.

The body 142 forms a substantially hollow structure, wherein the first end 140 is open to the atmosphere and able to be in fluid communication with a patient interface 1, and the second end 141 is a closed end. A "closed end" refers to there being a complete barrier over the end of body (such as over the end of the annular portion of the body) that prevents passage of fluid. The first end 140 is configured to fluidly couple with the patient interface 1, as previously described. The first end 140 is integrally formed with the body 142. The second end 141 is also integrally formed with the body 142.

The body 142 comprises at least two openings 155, 156. The at least two openings are configured to allow patient secretions to drain from the tracheostomy guard 10 in use. Each opening 155, 156 is circular, oval or some other suitable shape (oval is shown in the Figures). Each opening can have a different shape from the other opening. Preferably, one of the openings 155 is larger than the other opening 156 so that most of the secretions (e.g. sputum) will drain from that opening. The size of the opening 155 is bigger than the area of the interface opening such that any large particles ejected from the interface can also be ejected from the guard.

The tracheostomy guard 10 has a preferred orientation for connection to the patient interface 1 (also called a tracheostomy interface). When the tracheostomy guard 10 is connected to the interface 1 in the correct orientation, one of the two openings is orientated to face downwards, and the other of the openings is orientated to face upwards. This better controls the direction of drainage in a desired direction(s), compared to, for example, more openings where the secretions may drain in various undesired directions. For example, in use, the tracheostomy guard 10 of this embodiment is preferably attached to the patient interface 1 so that the smaller opening 156 is orientated upwards and the larger opening 155 is orientated downwards and extends nearer to the distal end/second end 141 of the guard 10 to allow most secretions to drain out easily. The smaller top opening 156 is mainly positioned away from the distal end 142 of the tracheostomy guard 10 so that the secretions hit the closed end 142 and change direction. Positioning the smaller opening 146 further from the distal end means it is less likely that the secretions will be projected through the smaller opening 156 after they reach the closed end 142 and change direction. By having more of the upper side closed and more of the lower side open, secretions are likely to be deflected downwards and therefore drain through the large opening 155 on the lower side (and onto a protective sheet on the chest of the patient or similar).

The above is only a preferred orientation, and is not essential. The orientation of the openings 155, 156 could be reversed, for example (deliberately or inadvertently). In this case, the smaller opening 156 prevents occlusion of the interface by secretions if put on upside down. It reduces occlusion of the interface if orientated upside down by allowing some amount of secretion to pass through. Also, alternatively, the openings 155, 156 could be the same size and shape, but they may not be as effective at controlling the direction of the secretions.

The second end 141 of the guard 10 preferably has arrows, logo, markings or some other indicia that assist the user to orientate the guard, and in particular the openings, and the correct manner to optimise drainage of secretions. The closed/sealed second end 141 of the guard, along with its curved shape helps redirect secretions towards the patient rather than the caregiver.

Like for the multiple openings in the first embodiment, the two openings 155, 156 in this embodiment can reduce the risk of occlusion or blockage at the patient interface 1 and can be positioned to reduce that risk, as described in the previous embodiment. The at least two openings can also be configured to provide access to a suction tube, in the same manner as described for the previous embodiment The size, shape and quantity of the openings 155, 156 can be altered without departing from the scope of the disclosure. Like the previous embodiment, the tracheostomy guard 10 of this embodiment is a disposable component and the same aesthetic and communication features as described for the previous embodiment can be applied to this embodiment.

Figure 21:
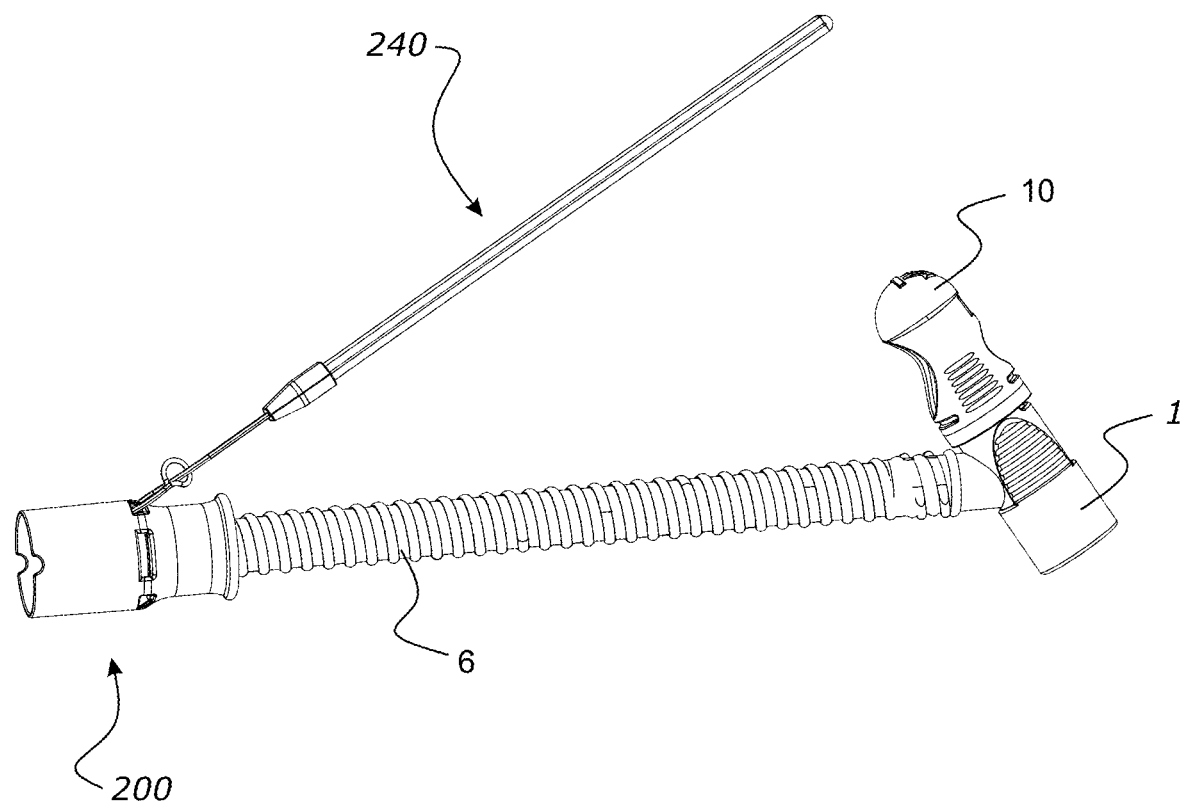
FIG. 21 shows an assembly of a connector, a tube, a tracheostomy interface, and a tracheostomy guard.

With reference to FIG. 21, there is shown an assembly comprising a tracheostomy guard as described above. The assembly may additionally comprise a tube 6 and a connector 200. Those components are described in more detail below.

The tube 6 may primarily comprise an inlet, an outlet, and an enclosing wall defining a gases passageway between said inlet and said outlet. At least a region of said wall comprises a membrane that is of a breathable material so as to allow the passage of water vapour without allowing the passage of liquid water or respiratory gases. Preferably substantially the entire length of the tube 6 is configured to allow the passage of water vapour without allowing the passage of liquid water or respiratory gases.

As used herein, the term "breathable" generally means highly permeable to water vapor and substantially impermeable to liquid water and the bulk flow of gases. A "breathable material" as used herein generally refers to a material that is highly permeable to water vapor and substantially impermeable to liquid water and the bulk flow of gases.

The tube 6 may include at least one helically wound polymer tape or strip, part or all of said strip comprising the membrane, respective edges of adjacent turns of said strip being adjoining or overlapping and bonded to form the enclosing wall.

One possible material for the breathable regions is an activated perfluorinated polymer material having extreme hydrophilic properties. An example of this polymer material is marketed under the trade name NAFION® by DuPont Fluoro products of Fayetteville USA. This material is useful due to its extreme hydrophilic properties and due to its ability to be extruded, particularly to be co-extruded in combination with other plastic materials.

Alternative materials include:

(a) Hydrophilic thermoplastics, (b) Woven treated fabric products exhibiting breathable characteristics.

A particularly suitable material is a hydrophilic polyester block copolymer formed into a homogeneous flat film. An example of such a film is sold under the brand SYMPATEX®. This material is particularly suited to thin film productions.

The tube 6 may include lateral reinforcement against deformation of the breathing gas conduit, such as a helical bead disposed over said adjoining or overlapping edges between turns of strip, or a series of annular ring beads or ribs distributed over the length of said conduit. The bead may be formed from a thermoplastic, and is preferably made of a polyester based polymer. The tape or strip and bead may both be polyester based polymers, which improves the bond between them. The bead may be made of a material sold under the trade name Arnitel® EM550.

The tube 6 may further or alternatively include longitudinal reinforcement against stretching of the tube 6.

The assembly also includes a lanyard 240. The lanyard 240 may be fastened or engaged to the connector 200. The lanyard 240 comprises a looped portion which can be fastened around a part of the connector 200 and then pulled through itself to securely associate the lanyard 240 to the connector 200. The lanyard 240 can then be placed around a user's neck, or a feature of the environment to take or support at least some of the weight of the connector 200, tube 6, tracheostomy guard 10 and/or tracheostomy interface 1.

Various alternatives to the embodiments described above could be envisaged. Some are described below, although these are not exhaustive.

In one alternative, the tracheostomy guard 10 could be inserted into the patient interface port 4. In this alternative, there could be a rib or other complementary feature on the inside of the patient interface port 4 for engagement with the tracheostomy guard coupling region 147. The force could be applied to coerce the tracheostomy guard opening into a shape configured for insertion into the port 4.

In another alternative, the tracheostomy guard 10 has a push fit coupling region configuration for coupling to the patient interface, like that described in the first embodiment, but a squeeze release coupling configuration like that described in the second embodiment. Other combinations of the first and second embodiments are also possible. The tracheostomy guard 10 could also be attached in other ways, such as with a helical thread. The tracheostomy guard 10 could attached via threading over or threading into the patient interface 1.

Experimental Data

Tests on various non-limiting examples of a tracheostomy guard were carried out, which show performance of the tracheostomy guard in relation to connection and disconnection from the patient interface. The dimensions of the test tracheostomy guards are examples only, and the invention can work on a wide range of dimensions, beyond those tested. All samples C to E produced acceptable results.

Tests have been carried out on tracheostomy guard samples (as described herein) with various wall thickness at the coupling region 147. The wall thicknesses vary between 0.5 and 2 mm. The thicknesses for the following samples are:

Sample C—1.25 mm
Sample D—1.5 mm
Sample E—1.75 mm on two sides where the squeezing force is applied and 1.5 mm on the deforming regions.

From this testing it appears the design D is the most favourable, while all designs were acceptable. The preferred thickness is between 1-1.8 mm, or more preferably between 1.4-1.5 mm.

In addition, it has been determined from testing that the preferred detachment force when intentionally detaching the guard from the interface ranges between 10 N-36 N. Sample C requires lower forces to facilitate detachment and Sample E requires the higher forces for detachment. Accidental detachment forces for Samples C-E were tested and measured against existing tracheostomy guards, showing that required forces to accidentally detach the new samples are substantially higher than the existing tracheostomy guards. A vertical force of ≤1.7 N and a side force of ≤6.5 N were required to accidentally detach the existing tracheostomy guards. The new samples C to E required vertical forces between 18 N-50 N, and side forces of 8 N-18 N to accidentally detach the guard from the interface.

What is claimed is:

1. A tracheostomy guard for a patient interface comprising:
    a body with a first end with an opening for coupling to or communicating with a patient interface, a second closed end, and a longitudinal axis extending through the first end and the second closed end;
    wherein the body further comprises a first opening a second opening distinct from the first opening, the first opening and the second opening positioned between the first open end and the second closed end, the first opening and the second opening are configured to drain waste from the tracheostomy guard; and
    wherein the first opening is larger than the second opening;
    wherein an axis perpendicular to the longitudinal axis extends through the first opening and the second opening.

2. A tracheostomy guard for a patient interface according to claim 1, wherein the body is frustoconical or cylindrical.

3. A tracheostomy guard for a patient interface according to claim 1, wherein the second closed end is rounded.

4. A tracheostomy guard for a patient interface according to claim 1, wherein the body tapers from the first open end to the second closed end.

5. A tracheostomy guard for a patient interface according to claim 1, wherein the first opening is configured to face toward a chest of the patient when assembled on the patient interface.

6. A tracheostomy guard for a patient interface according to claim 1, wherein each of the first opening and the second opening is elliptical or circular.

7. A tracheostomy guard for a patient interface according to claim 1, further comprising an indicator for guiding assembly with the patient interface, wherein the indicator comprises one or more arrows that guide positioning of the first opening and the second opening upon assembly.

8. An assembly comprising a tracheostomy guard according to claim 1, coupled to a patient interface and wherein the patient interface is or comprises a tracheal interface.

9. An assembly according to claim 8, further comprising a tube for delivery of gases to the patient interface.

10. An assembly according to claim 9, wherein the tube is permeable to water vapour and the tube is impermeable to liquid water or bulk flow of gases.

11. An assembly according to claim 8, wherein a first end of the patient interface is configured or configurable to fluidly connect with the airway of a patient and a second end of the patient interface is configured or configurable to couple with the tracheostomy guard.

12. An assembly according to claim 10, further comprising a connector for connecting a first end of the tube with a gases delivery conduit.

13. A tracheostomy guard for a patient interface according to claim 1, wherein each of the first opening and the second opening extends through an outermost wall of the body.

14. A tracheostomy guard for a patient interface according to claim 1, wherein the first opening is on an opposite side of the body from the second opening.

15. A tracheostomy guard for a patient interface comprising:
- a body with a first end with an opening, a second closed end, the body further comprising a first opening and a second opening positioned between the first end and the second closed end, the first opening and the second opening configured to drain waste from the tracheostomy guard,
- wherein the first end opening is biased into a first configuration, and on application of a force the first end opening is configured to be manipulated into a second configuration, and
- wherein, in the second configuration, the first end opening is shaped to facilitate coupling a port of a patient interface, and once coupled and after release of the force, the first end opening biases into or at least towards the first configuration which is shaped to retain the tracheostomy guard on the patient interface.

16. A tracheostomy guard for a patient interface according to claim 15, wherein in the first configuration, the first end opening is elongated.

17. A tracheostomy guard for a patient interface according to claim 15, wherein in the first configuration, the first end opening is oval, with a major axis and a minor axis, configured such that upon application of the force the major axis decreases and minor axis increases in length to manipulate the first end opening into the second configuration.

18. A tracheostomy guard for a patient interface according to claim 17, wherein, the body in line with the major axis of the first end, or the major axis of the first end opening, is configured to receive the application of force.

19. A tracheostomy guard for a patient interface according to claim 15, wherein, in the second configuration, the first end opening is circular or near circular.

20. A tracheostomy guard for a patient interface according to claim 15, wherein the body comprises one or more slots.

21. A tracheostomy guard for a patient interface according to claim 20, wherein the one or more slots are at or near the first end of the opening.

22. A tracheostomy guard for a patient interface according to claim 15, further comprising one or more ribs to provide one or more internal stops and/or to provide one or more support structures.

23. A tracheostomy guard for a patient interface according to claim 15, wherein a force application region is configured to receive the application of force and the force application region is or has a grip.

* * * * *